United States Patent
Bae et al.

(10) Patent No.: US 12,329,866 B2
(45) Date of Patent: Jun. 17, 2025

(54) SELECTIVE SMART AIR-SURFACE STERILIZATION SYSTEM BASED ON OCCUPIED SITUATION AND EMPTY SITUATION

(71) Applicant: KOREA INSTITUTE OF CIVIL ENGINEERING AND BUILDING TECHNOLOGY, Gyeonggi-do (KR)

(72) Inventors: Sang-Hwan Bae, Incheon (KR); Jung-Yeon Yu, Seoul (KR)

(73) Assignee: KOREA INSTITUTE OF CIVIL ENGINEERING AND BUILDING TECHNOLOGY, Goyang-si (KR)

( * ) Notice: Subject to any disclaimer, the term of this patent is extended or adjusted under 35 U.S.C. 154(b) by 452 days.

(21) Appl. No.: 17/989,735

(22) Filed: Nov. 18, 2022

(65) Prior Publication Data

US 2023/0310673 A1 Oct. 5, 2023

(30) Foreign Application Priority Data

Apr. 5, 2022 (KR) ........................ 10-2022-0042224

(51) Int. Cl.

| | | |
|---|---|---|
| A61L 2/10 | (2006.01) | |
| A61L 2/26 | (2006.01) | |
| A61L 9/20 | (2006.01) | |
| B66B 11/02 | (2006.01) | |
| F24F 8/22 | (2021.01) | |
| F24F 13/20 | (2006.01) | |

(52) U.S. Cl.
CPC .................. *A61L 2/10* (2013.01); *A61L 2/26* (2013.01); *A61L 9/20* (2013.01); *F24F 8/22* (2021.01); *F24F 13/20* (2013.01); *A61L 2202/11* (2013.01); *A61L 2202/14* (2013.01); *A61L 2202/25* (2013.01); *A61L 2209/111* (2013.01); *A61L 2209/12* (2013.01); *A61L 2209/15* (2013.01); *B66B 11/0226* (2013.01)

(58) Field of Classification Search
None
See application file for complete search history.

(56) References Cited

U.S. PATENT DOCUMENTS

2022/0111105 A1\* 4/2022 Pan ........................... A61L 9/20

FOREIGN PATENT DOCUMENTS

| CN | 105502134 A | \* | 4/2016 | | |
|---|---|---|---|---|---|
| CN | 111252649 A | \* | 6/2020 | ............... | A61L 2/10 |
| CN | 212880215 U | | 4/2021 | | |
| CN | 111252649 B | \* | 7/2021 | ............... | A61L 2/10 |
| KR | 10-1702067 B1 | | 2/2017 | | |
| KR | 10-2020-0019338 A | | 2/2020 | | |
| KR | 10-2021-0144558 A | | 11/2021 | | |

\* cited by examiner

*Primary Examiner* — Andrew Smyth
(74) *Attorney, Agent, or Firm* — Goldilocks Zone IP Law

(57) ABSTRACT

A smart air-surface sterilization system of the present disclosure automatically determines an occupied situation or an empty situation of an indoor space and performs air sterilization using Ultra-Violet C (UVC) in the occupied situation and surface sterilization using UVC in the empty situation.

4 Claims, 19 Drawing Sheets

SELECTIVE SMART AIR-SURFACE STERILIZATION SYSTEM BASED ON OCCUPIED SITUATION AND EMPTY SITUATION

CROSS-REFERENCE TO RELATED APPLICATION

This application claims priority to Korean Patent Application No. 10-2022-004224, filed on Apr. 5, 2022, and all the benefits accruing therefrom under 35 U.S.C. § 119, the contents of which in its entirety are herein incorporated by reference.

BACKGROUND

1. Field

The present disclosure relates to a system for sterilization of an indoor space by Ultra-Violet C (UVC) radiation.

2. Description of the Related Art

It is necessary to sterilize and disinfect an indoor space where people enter and leave such as an office, an elevator car and a room for extracting medical specimens. For sterilization and disinfection, Ultra-Violet C (UVC) radiation may be used.

The UVC radiation is used for sterilization of air in the indoor space, i.e., "air sterilization". Additionally, the UVC radiation may be used for sterilization of surfaces in the indoor space such as walls or touch panels, i.e., "surface sterilization".

When the human body is directly exposed to UVC, it may cause vision loss or skin cancers. Accordingly, when sterilizing the indoor space using UVC, it is necessary to prevent the direct exposure of the human body to UVC. The sterilization effects (sterilization capacity) of UVC may differ depending on the amount of light, the exposure time and the irradiation distance. As UVC radiation is emitted at a longer distance, the sterilization capacity is lower. Accordingly, to maximize the sterilization effect using UVC, it is necessary to reduce the distance between a UVC lamp and a surface that UVC strikes as much as possible. The indoor space is occupied when someone is in the indoor space or is empty when no one is in the indoor space. Accordingly, when sterilizing the indoor space using UVC, it is desirable to sterilize the indoor space depending on the occupied situation or the empty situation of the indoor space.

SUMMARY

The present disclosure is directed to providing sterilization of an indoor space using Ultra-Violet C (UVC).

In particular, the present disclosure is directed to providing sterilization technology that automatically determines whether the indoor space is in an occupied situation or an empty situation, and sterilizes the indoor space in different ways depending on the situation of the indoor space.

The present disclosure is directed to providing an apparatus that only performs air sterilization using UVC in the occupied situation of the indoor space and performs surface sterilization using UVC in the empty situation.

The present disclosure is directed to providing the apparatus for sterilizing the indoor space with the maximized sterilization effect by increasing the exposure time of the indoor space to UVC while preventing the direct exposure of the human body to UVC and reducing the UVC irradiation distance.

To achieve the above-described objective, the present disclosure provides a smart air-surface sterilization system including a human body detection sensor to detect the presence or absence of a person in an indoor space to determine an occupied situation or an empty situation; a lifting member installed on the ceiling of the indoor space; a lifting module to vertically lift the lifting member up and down in the indoor space; a folding module installed on the upper surface of the lifting member, wherein the folding module is folded when the lifting member is lifted up and is unfolded into a straight line shape when the lifting member is lifted down; a UVC lamp installed in the folding module to emit UVC radiation; and an air circulation fan to circulate air in the indoor space, wherein when the human body detection sensor determines the empty situation, the lifting member is vertically lifted down close to the bottom surface of the indoor space by the operation of the lifting module, the folding module is unfolded and vertically extended and subsequently the UVC lamp is also vertically extended to emit UVC radiation onto the wall of the indoor space to perform surface sterilization, and when the human body detection sensor determines the occupied situation, the lifting member is lifted up to a location close to the ceiling surface by the operation of the lifting module, the folding module is folded and the UVC lamp faces the ceiling surface of the indoor space, and then the air circulation fan operates to allow air to flow between the upper surface of the lifting member and the ceiling surface of the indoor space and the UVC lamp emits UVC radiation to the flow of air to perform air sterilization.

The system of the present disclosure automatically determines the occupied situation or the empty situation of the indoor space and sterilizes the indoor space in different ways depending on the situation of the indoor space.

When the indoor space is in the occupied situation, the system of the present disclosure only performs air sterilization by emitting UVC radiation into the air in the indoor space while circulating the air. Accordingly, it is possible to prevent the direct exposure of the human body to UVC and avoid UVC hazard to the human body during the air sterilization using UVC.

When the indoor space is in the empty situation, the present disclosure performs surface sterilization by emitting UVC radiation close to the surface of the indoor space. The wall of the indoor space is always exposed to UVC while there is no one in the indoor space. Accordingly, it is possible to greatly increase the exposure time of the surface of the indoor space to UVC, thereby increasing the sterilization effect. Additionally, since the UVC lamp is placed close to the wall, it is possible to reduce the UVC irradiation distance, thereby maximizing the surface sterilization effect.

The present disclosure is very useful in indoor spaces where people enter and leave such as offices, elevator cars and rooms for extracting medical specimens.

DETAILED DESCRIPTION

Hereinafter, an exemplary embodiment of the present disclosure will be described with reference to the accompanying drawings. Although the present disclosure is described with reference to the embodiment shown in the accompanying drawings, the description is made as an embodiment, and the technical spirit of the present disclosure and the essential components and their operation are not limited thereto.

Figure 1:
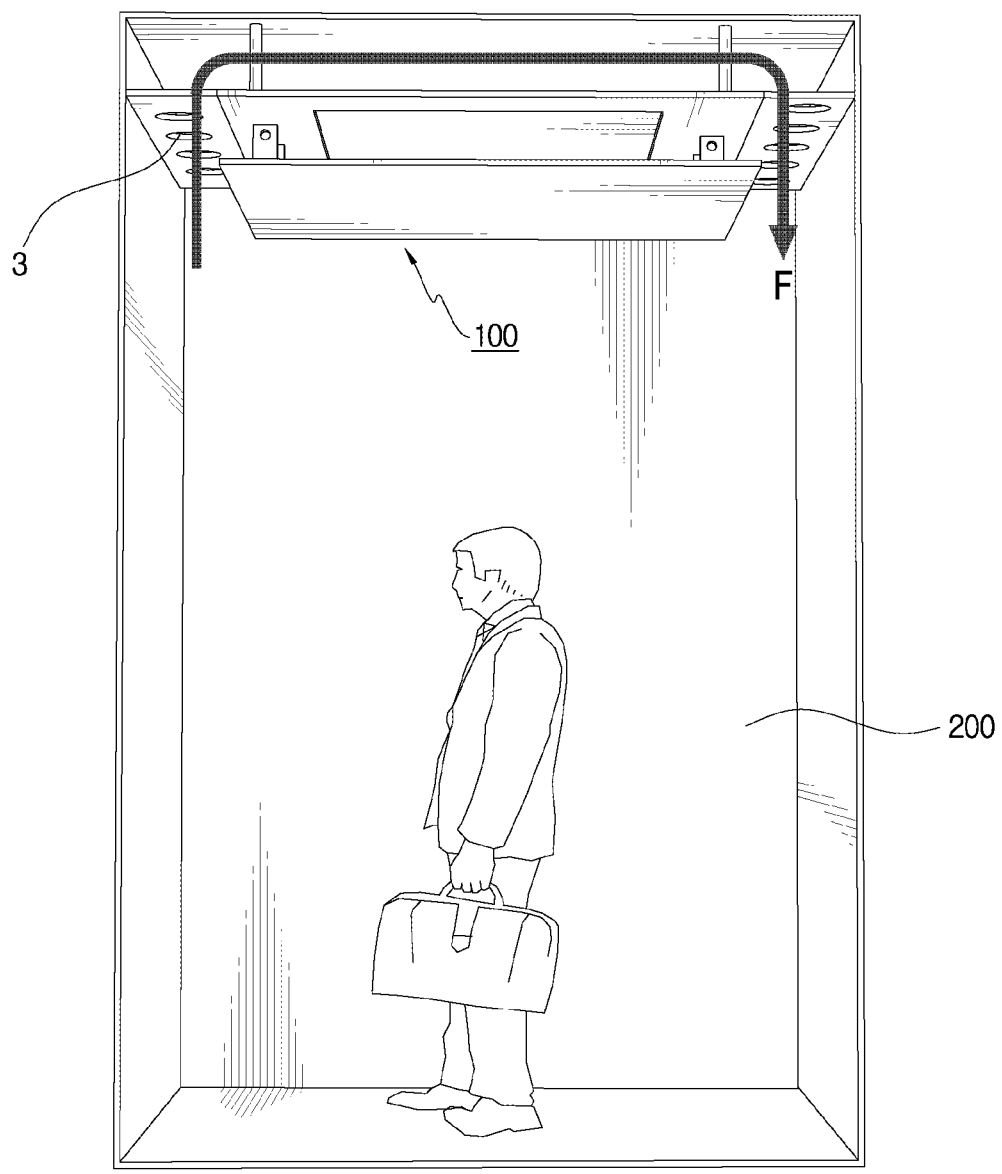
FIG. 1 is a schematic perspective view showing the operation of a sterilization system according to the present disclosure in an occupied situation.
Figure 2:
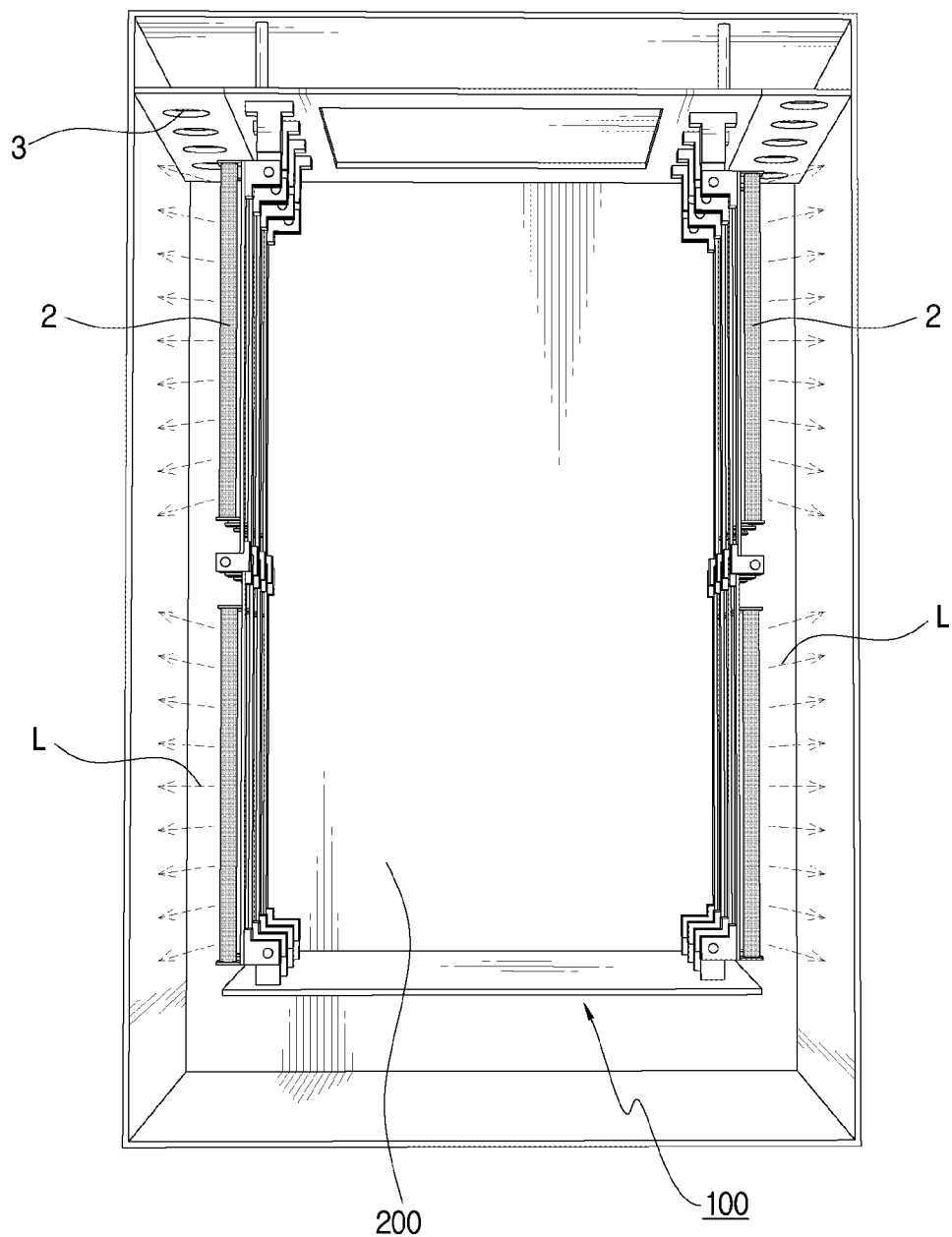
FIG. 2 is a schematic perspective view showing the operation of a sterilization system according to the present disclosure in an empty situation.
Figure 3:
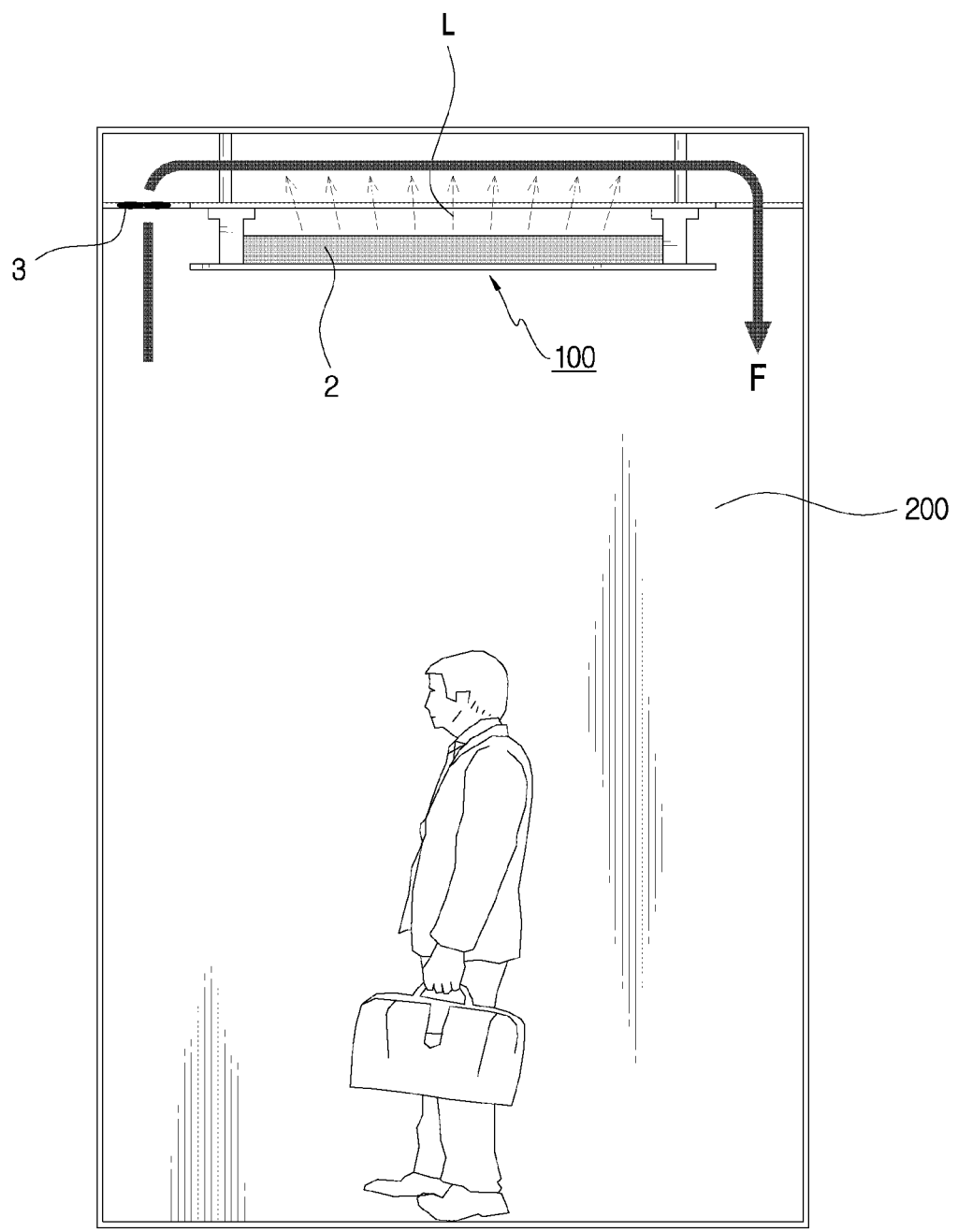
FIG. 3 is a schematic side view of the situation of FIG. 1.
Figure 4:
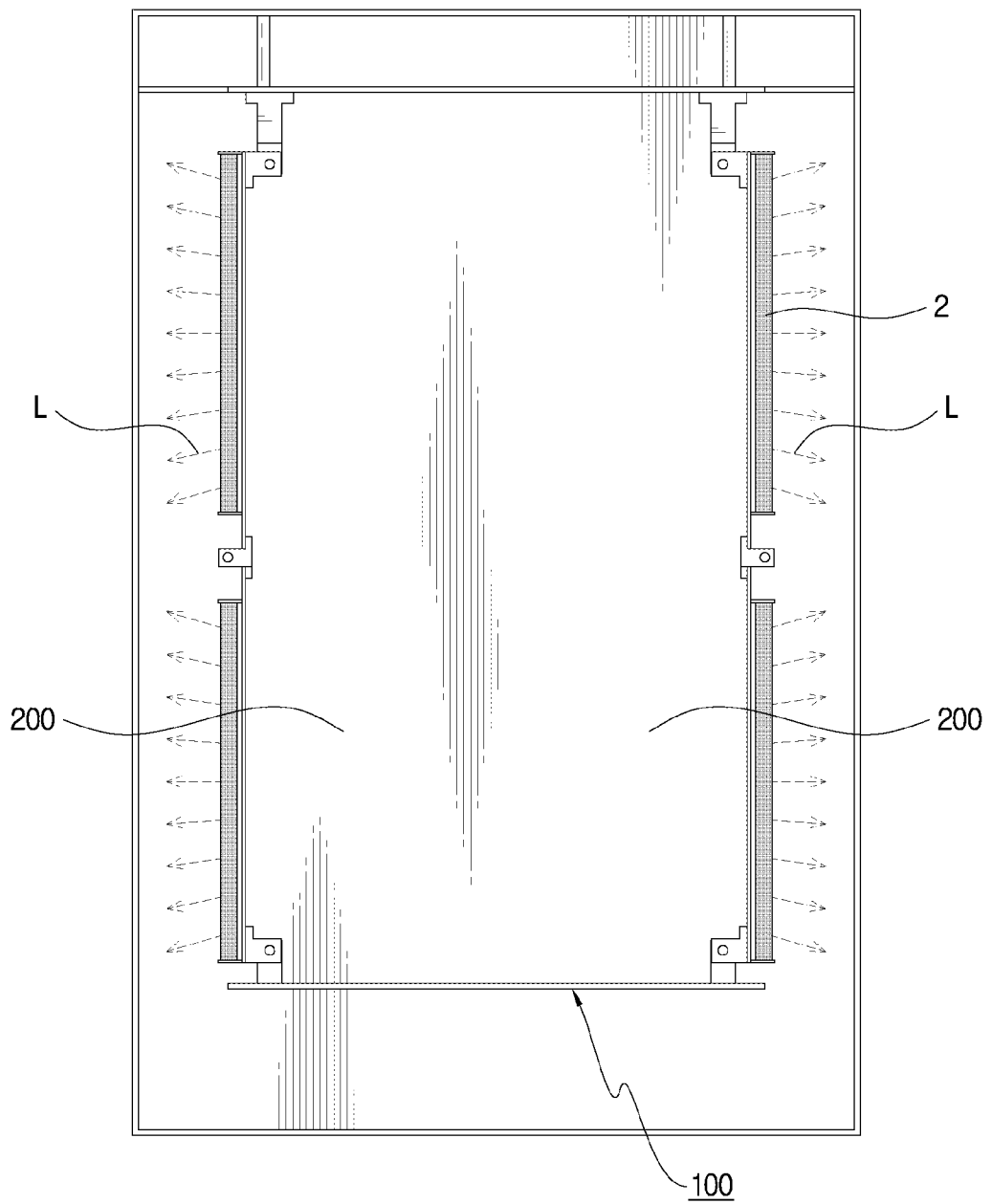
FIG. 4 is a schematic side view of the situation of FIG. 2.

FIGS. 1 and 2 are schematic perspective views, each showing the operation of a smart air-surface sterilization system 100 according to the present disclosure installed in an elevator car as an example of an indoor space 200. FIG. 1 shows an occupied situation of the indoor space 200. FIG. 2 shows an empty situation of the indoor space 200. FIGS. 3 and 4 are schematic side views of the situations of FIGS. 1 and 2, respectively.

The smart air-surface sterilization system 100 is installed in the indoor space. The indoor space refers to a space where people enter and leave such as an office, an elevator car and a room for extracting medical specimens. The smart air-surface sterilization system 100 senses the presence or absence of a person in the indoor space. The occupied situation of the indoor space refers to a situation in which someone is in the indoor space 200. The empty situation of the indoor space refers to a situation in which there is no one in the indoor space 200. In the occupied situation of the indoor space, the smart air-surface sterilization system 100 performs sterilization of air in the indoor space, i.e., air sterilization. In the empty situation of the indoor space, the smart air-surface sterilization system 100 performs sterilization of surfaces in the indoor space, i.e., surface sterilization. The surface sterilization may be performed in parallel with air sterilization.

The smart air-surface sterilization system 100 includes a human body detection sensor, a lifting member 1, a lifting module, a folding module, a Ultra-Violet C (UVC) lamp 2 and a control module. The smart air-surface sterilization system 100 may further an air circulation fan 3 if necessary.

The human body detection sensor detects the presence or absence of a person in the indoor space. The human body detection sensor may be disposed in the lifting member 1. The human body detection sensor may be installed at any other location that makes it easy to detect the presence or absence of a person in the indoor space. A signal measured by the human body detection sensor is transmitted to the control module by a wired/wireless method. The control module determines the occupied situation or the empty situation according to the signal from the human body detection sensor. The control module controls the operation of the components of the smart air-surface sterilization system 100 including the lifting module, the folding module, the UVC lamp, the lifting member, the human body detection sensor and the air circulation fan by a wired/wireless method.

The lifting member 1 is hung from the ceiling surface of the indoor space. The lifting module vertically lifts the lifting member 1 up or down. In the occupied situation of the indoor space, the lifting member 1 is lifted up not to interrupt the activities of users. When the lifting member 1 is lifted up, the lifting member 1 is located close to the ceiling surface of the indoor space, facing the ceiling surface at a predetermined distance apart. In the empty situation of the indoor space, the lifting member 1 is lifted down. When the lifting member 1 is lifted down, the lifting member 1 vertically moves down and is located close to the bottom surface of the indoor space.

The lifting member 1 has an upper surface that faces the ceiling surface of the indoor space. The folding module is installed on the upper surface of the lifting member 1. When the lifting member 1 is lifted up, the folding module is folded. When the lifting member 1 is lifted down, the folding module is unfolded. Accordingly, when the lifting member 1 is completely lifted down, the folding module is unfolded and vertically extended.

The UVC lamp 2 emits UVC radiation. The UVC lamp 2 is installed in the folding module. When the lifting member 1 is lifted up and the folding module is folded, the UVC lamp 2 faces the ceiling surface of the indoor space. When UVC radiation is emitted by the UVC lamp 2, air present in between the upper surface of the lifting member 1 and the ceiling surface of the indoor space is sterilized. The smart air-surface sterilization system 100 may further include the air circulation fan 3 if necessary. The air circulation fan 3 allows air in the indoor space to flow to the gap between the lifting member 1 and the ceiling surface of the indoor space. Accordingly, when the air circulation fan 3 operates, air in the indoor space is sucked toward the ceiling surface, flows between the upper surface of the lifting member 1 and the ceiling surface of the indoor space and is forced back down toward the indoor space. In this flow of air, the UVC lamp 2 operates to emit UVC radiation into the air flowing between the lifting member 1 and the ceiling surface of the indoor space to perform "air sterilization". In the occupied situation of the indoor space, air sterilization is performed in this way. In the occupied situation of the indoor space, the UVC lamp 2 is located near the ceiling surface of the indoor space and emits UVC radiation toward the ceiling surface. Accordingly, even though a person is present in the indoor space, UVC radiation is not harmful to the person. In FIGS. 1 to 4, the thick arrow F indicates the flow of air by the air circulation fan 3. In FIGS. 1 to 4, the small arrow L indicates the UVC radiation from the UVC lamp 2.

When it is determined that the indoor space is in the empty situation, the lifting member 1 is lifted down and the folding module is unfolded into a straight line shape. The lifting member 1 is located close to the bottom surface of the indoor space. When the folding module is unfolded into a straight line shape, the UVC lamp 2 is also placed in a straight line shape. Accordingly, the UVC lamp 2 faces the wall of the indoor space. The UVC lamp 2 operates to emit UVC radiation to the wall of the indoor space, to perform direct sterilization of the wall, i.e., "surface sterilization". When there is no one in the indoor space, the surface sterilization of the wall by UVC is performed. In this instance, when a person enters the indoor space, the human body detection sensor recognizes the human body and the smart air-surface sterilization system 100 determines the occupied situation of the indoor space. Accordingly, the folding module is folded, and the lifting member 1 is lifted up and located close to the ceiling surface. Additionally, the UVC lamp 2 faces the ceiling surface of the indoor space again. In this state, as described above, air sterilization is performed. UVC radiation is emitted into the air flowing between the upper surface of the lifting member 1 and the ceiling surface of the indoor space by the operation of the air circulation fan 3. Accordingly, the human body is not directly exposed to UVC and there is no UVC hazard to the human body.

When the indoor space is in the empty situation, surface sterilization is performed by emitting UVC radiation onto the surface of the indoor space such as the wall. The wall of the indoor space is always exposed to UVC while there is no one in the indoor space, and as the duration of exposure to UVC increases, the sterilization effect may increase. In the surface sterilization, the UVC lamp is disposed close to the wall. Accordingly, it is possible to reduce the UVC irradiation distance, thereby maximizing the surface sterilization effect using UVC.

Figure 5:
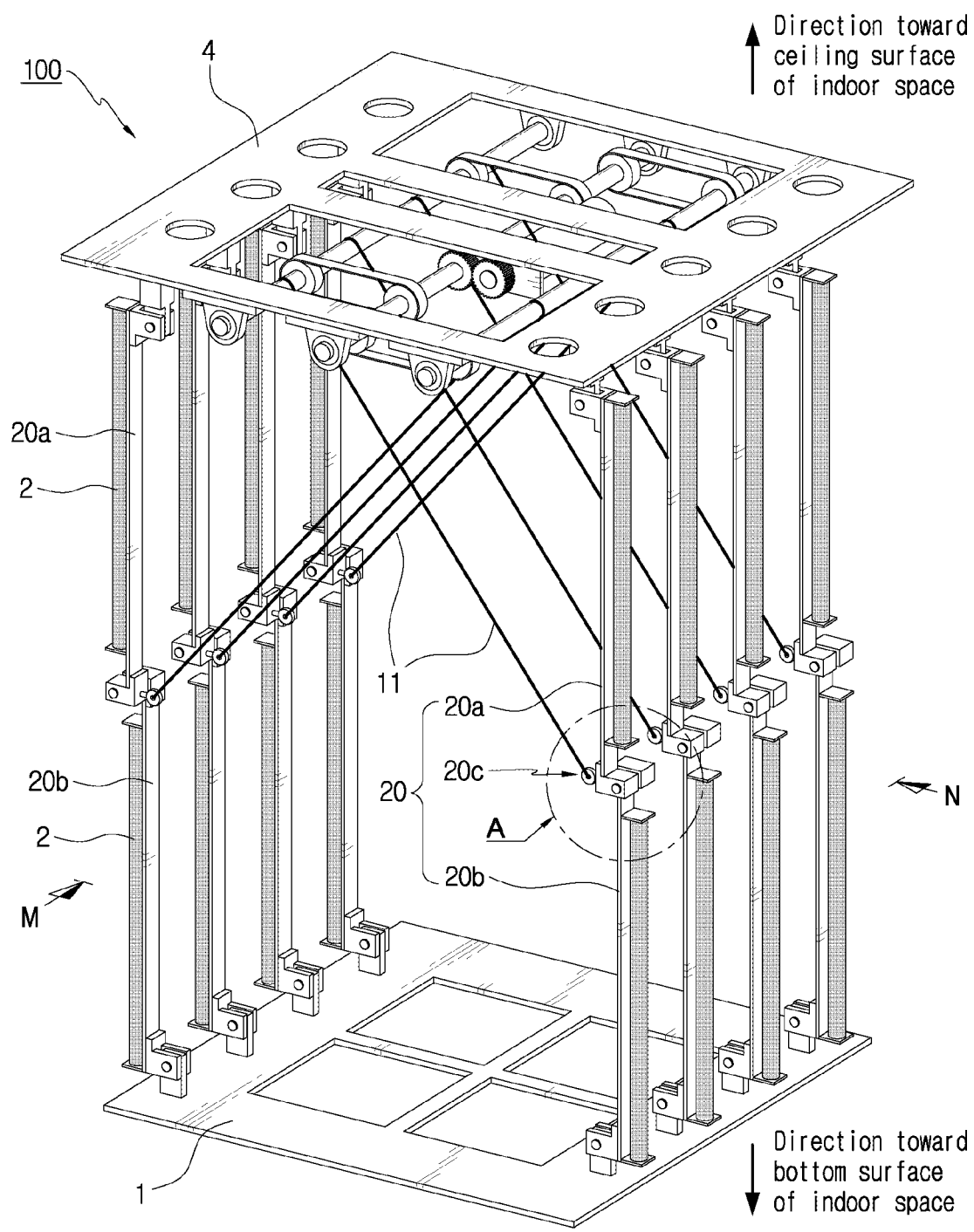
FIGS. 5 and 6 are schematic perspective views of a smart air-surface sterilization system of the present disclosure in a surface sterilization mode when viewed from different directions.
Figure 6:
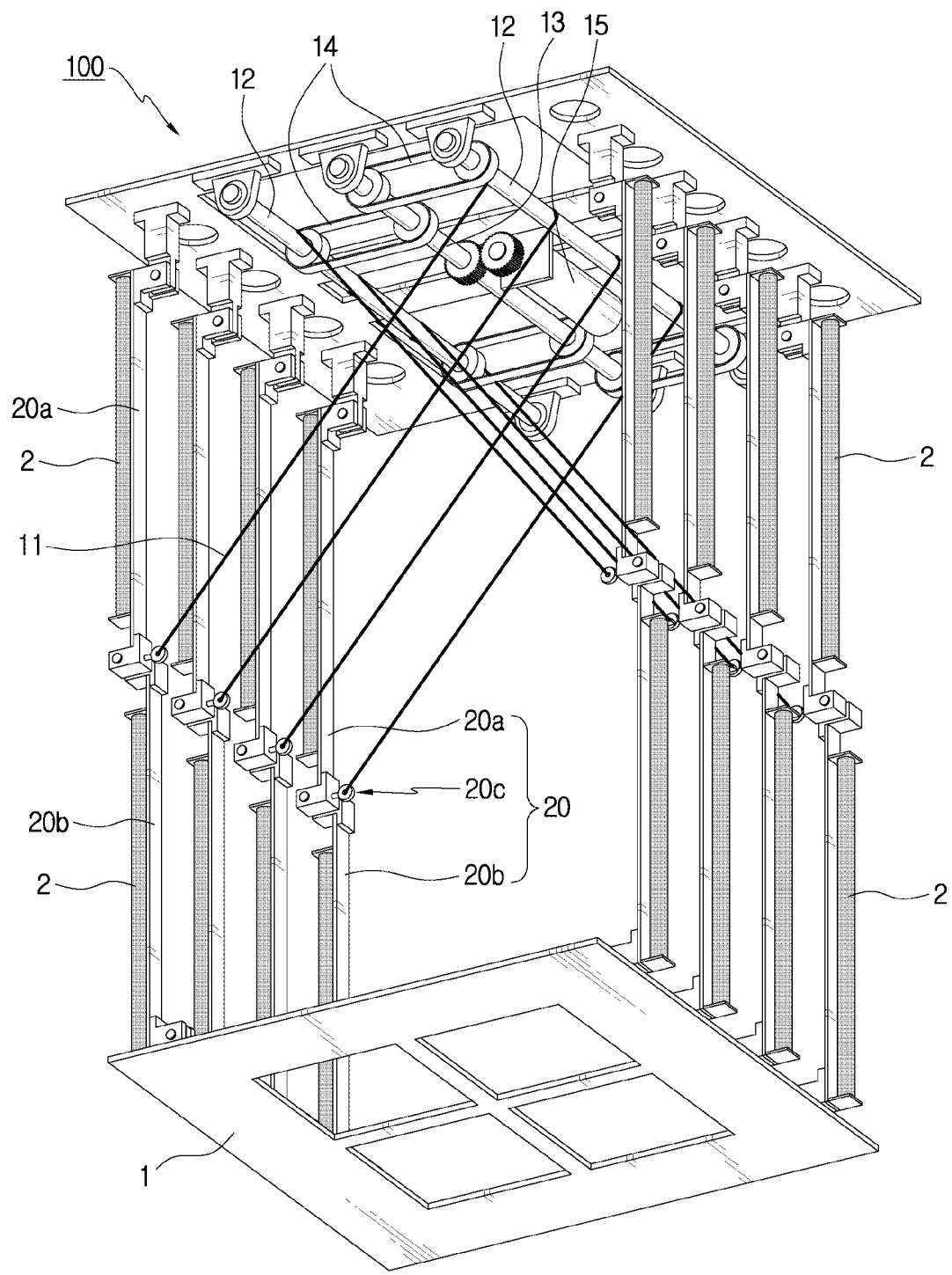
Figure 7:
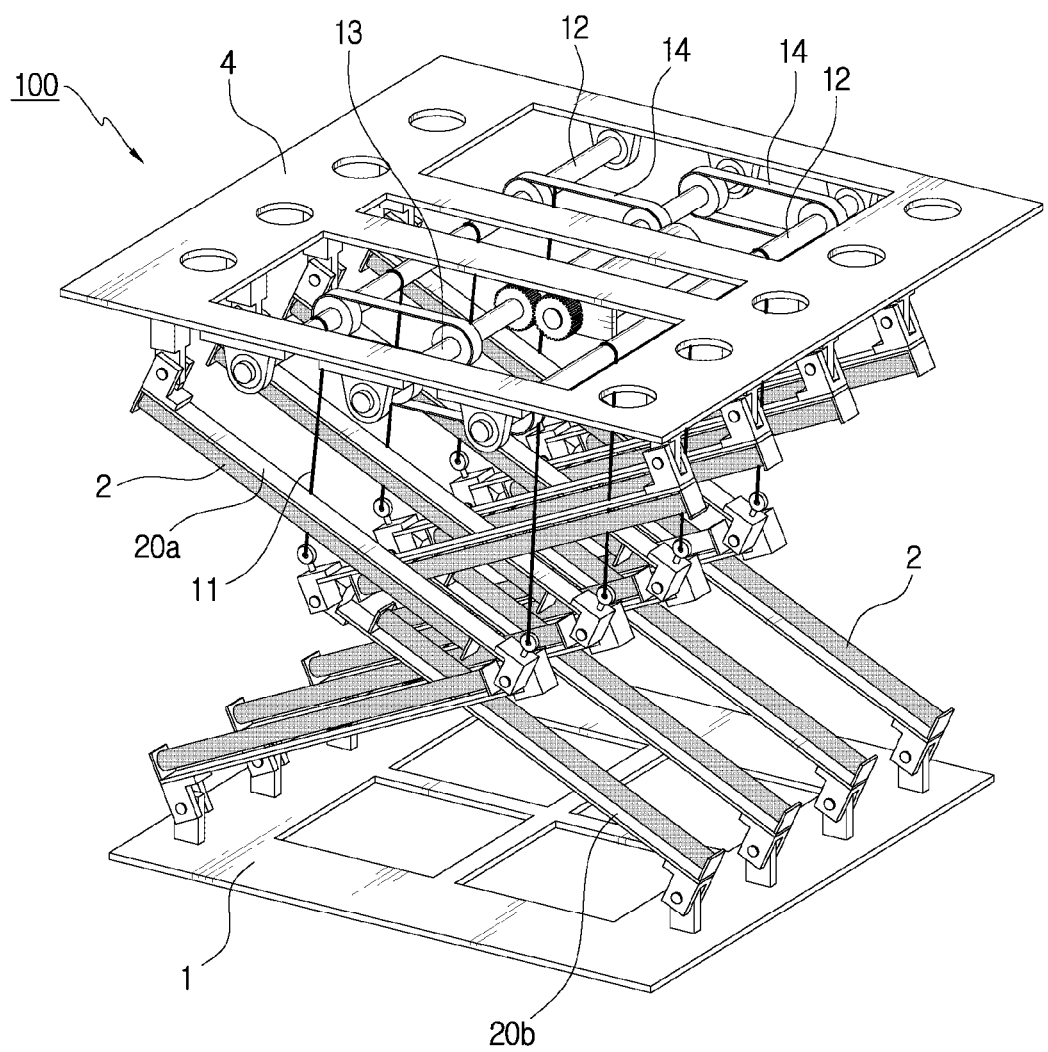
FIGS. 7 and 8 are schematic perspective views of a smart air-surface sterilization system of the present disclosure in a transition mode from a surface sterilization mode to an air sterilization mode when viewed from different directions.
Figure 8:
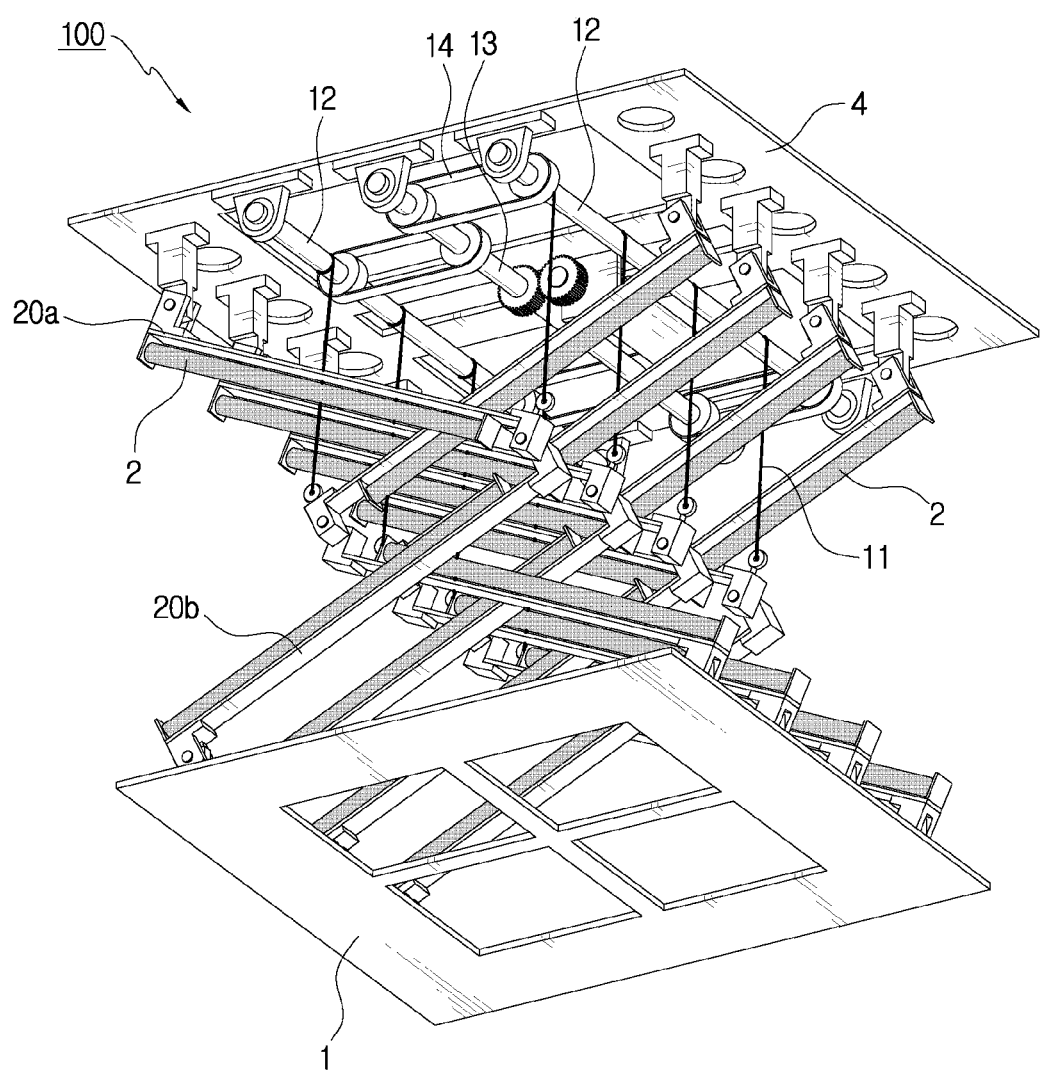
Figure 9:
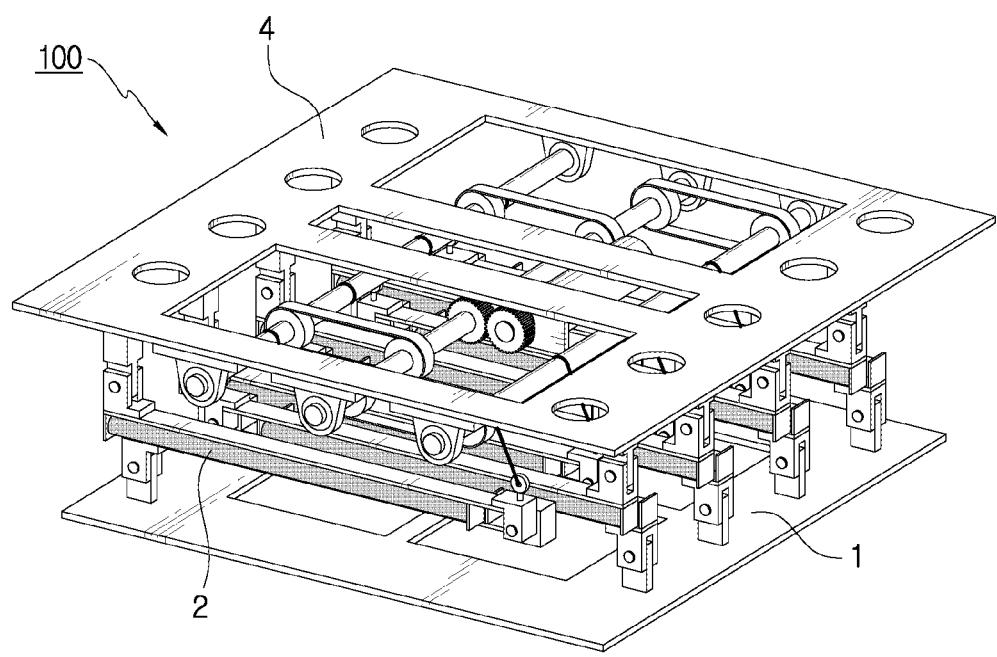
FIGS. 9 and 10 are schematic perspective views of a smart air-surface sterilization system of the present disclosure in an air sterilization mode when viewed from different directions.
Figure 10:
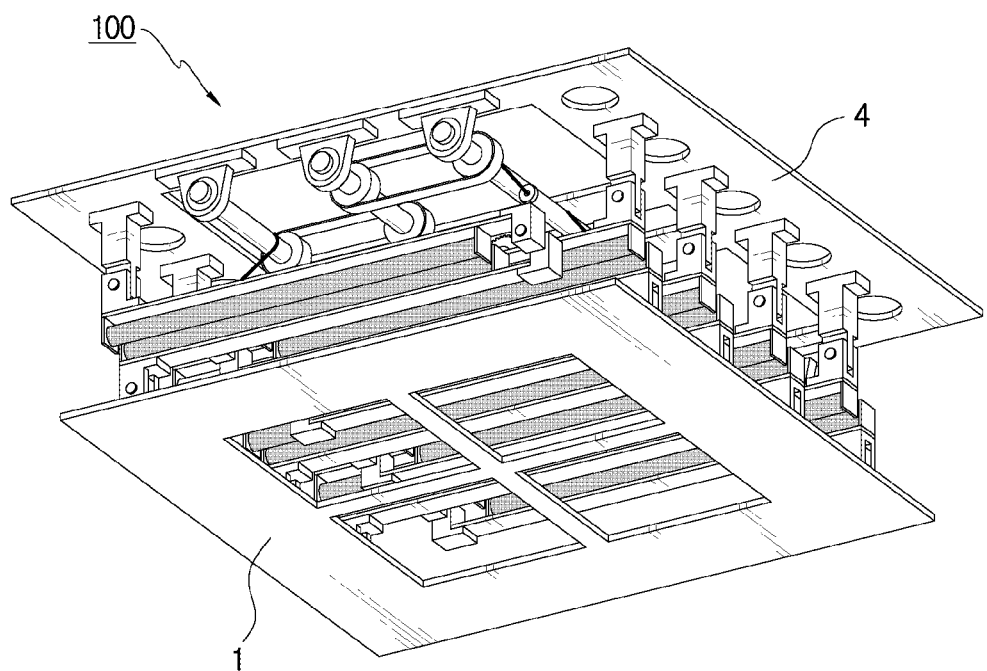
Figure 11:
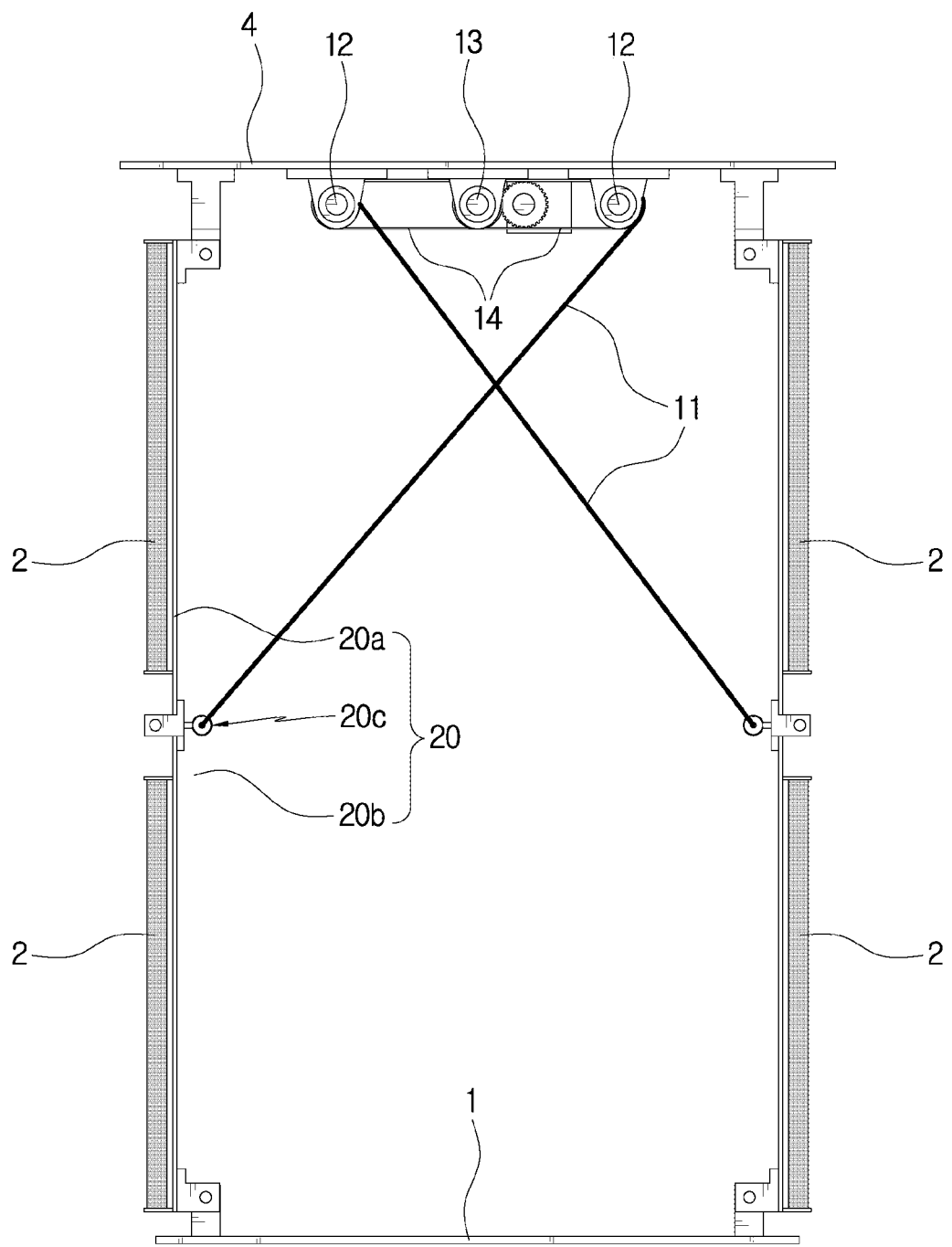
FIGS. 11 to 13 are schematic side views showing sequentially the transition from a surface sterilization mode to an air sterilization mode when viewed from the arrow direction M in FIG. 5.
Figure 12:
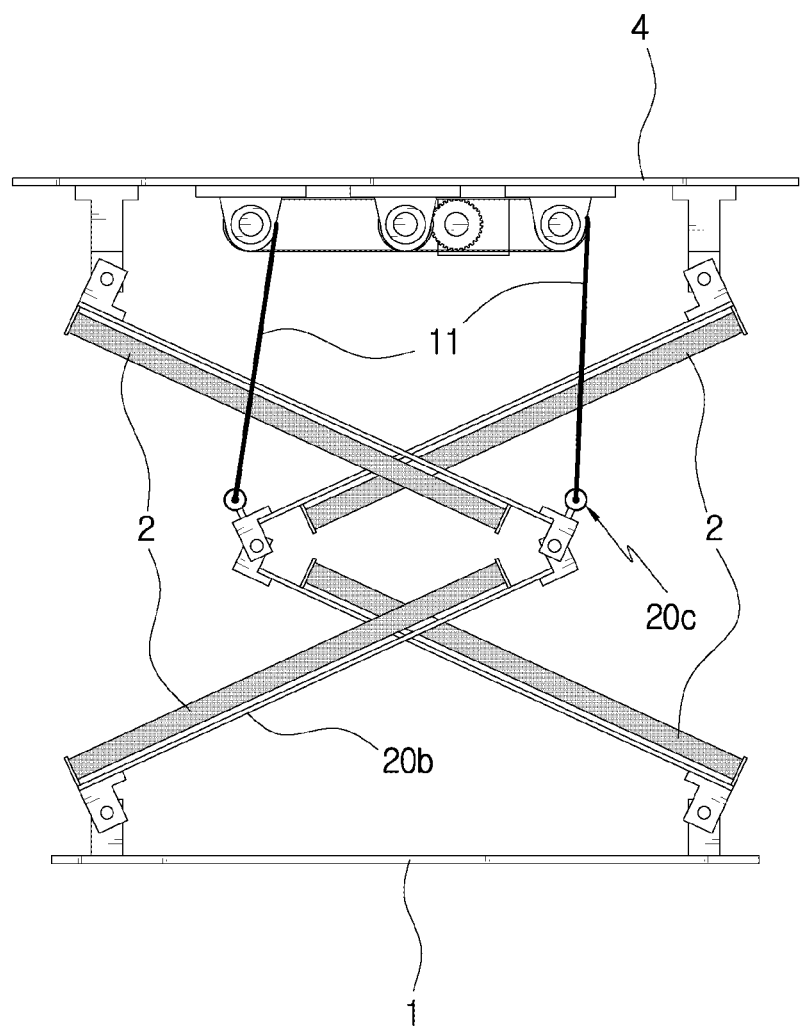
Figure 13:
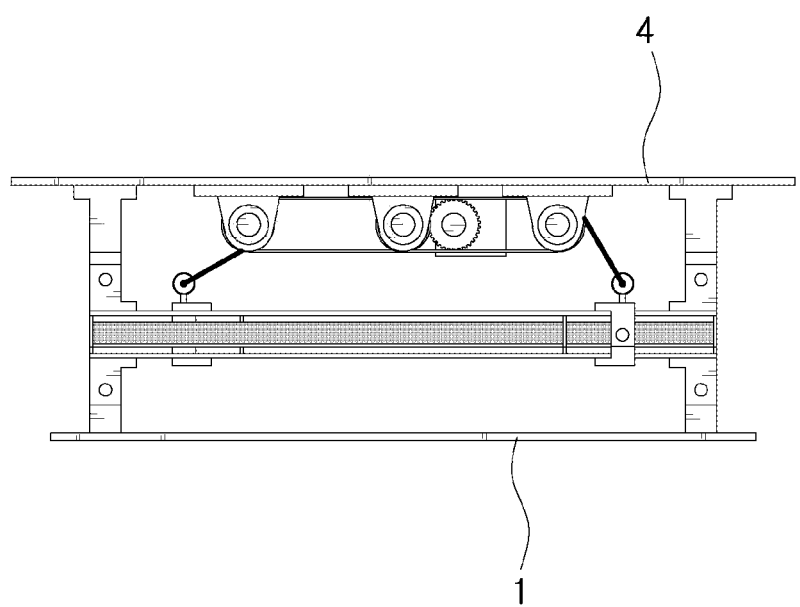
Figure 14:
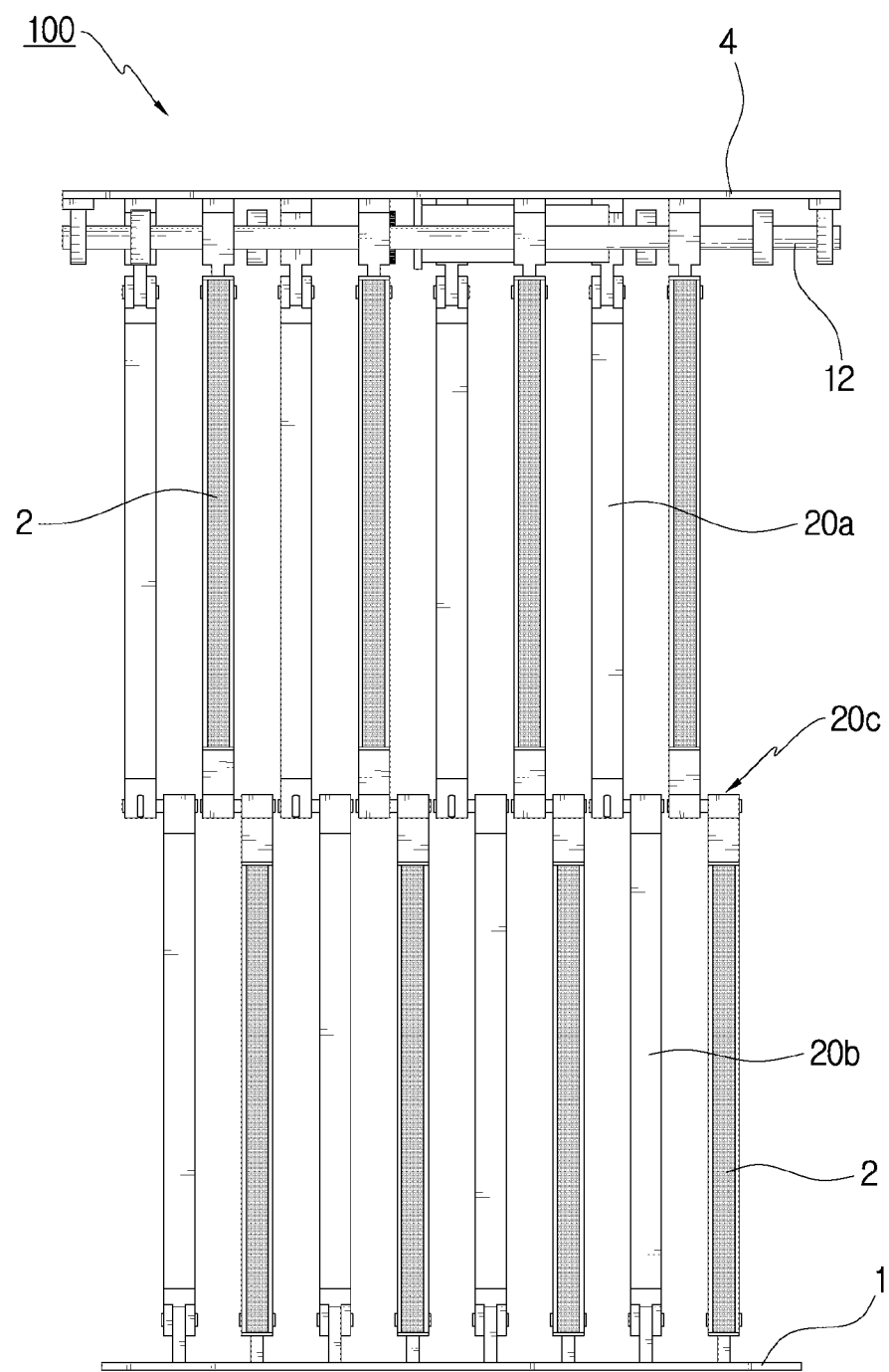
FIGS. 14 to 16 are schematic side views showing sequentially the transition from a surface sterilization mode to an air sterilization mode when viewed from the arrow direction N in FIG. 5.
Figure 15:
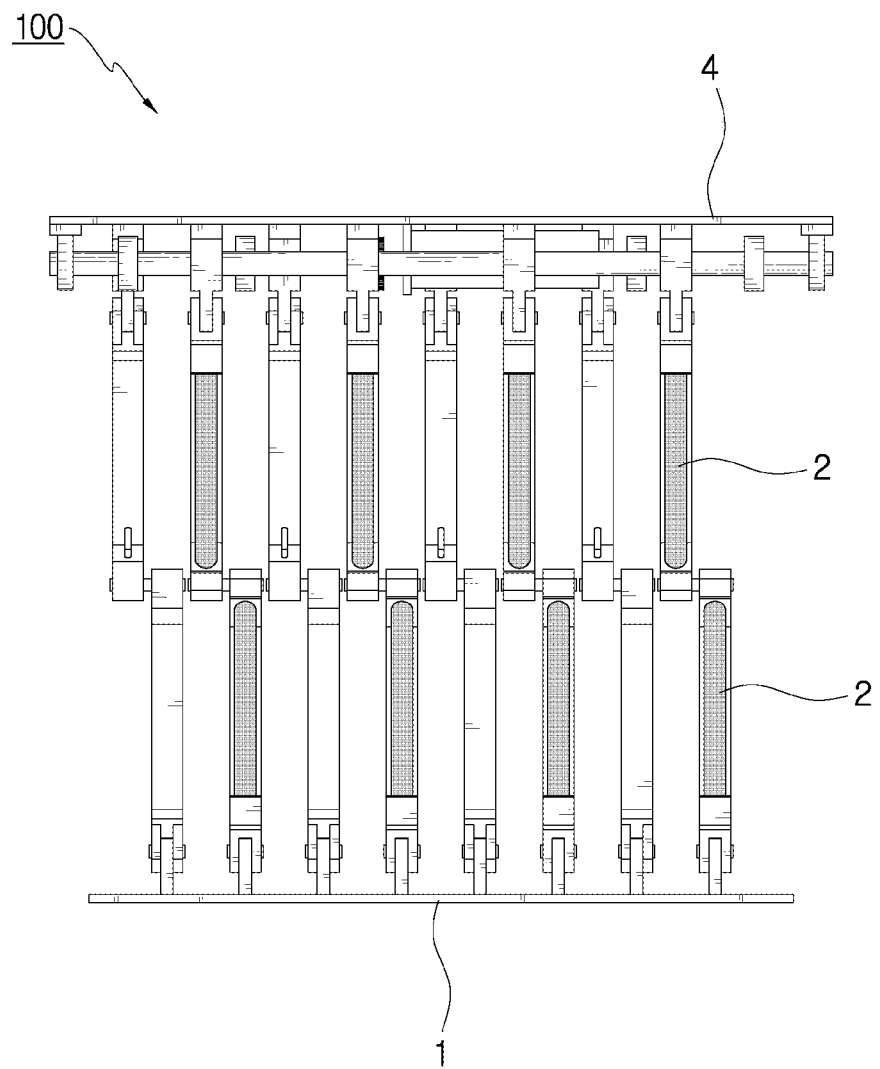
Figure 16:
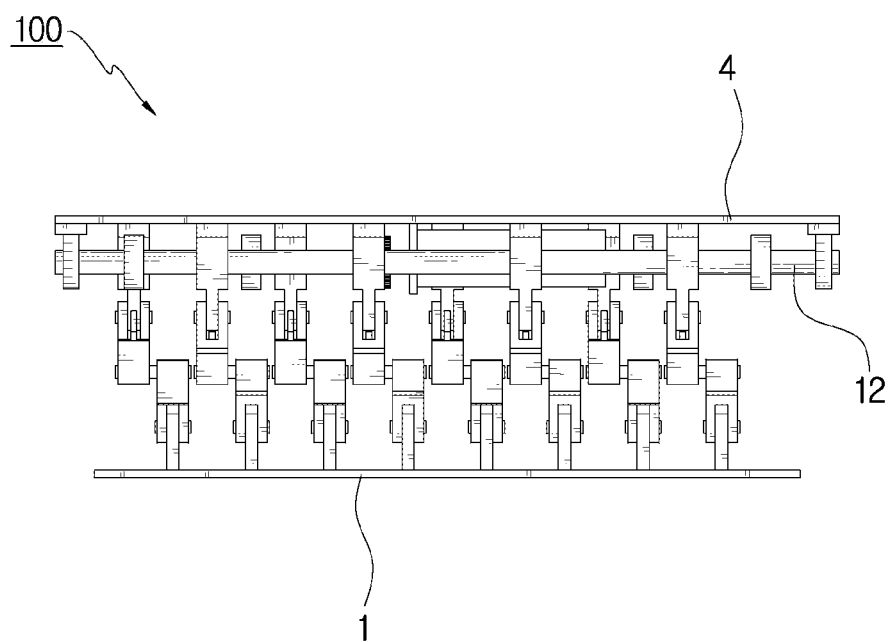

FIGS. 5 to 11 show an embodiment of the smart air-surface sterilization system 100 of the present disclosure in detail. FIGS. 5 and 6 are schematic perspective views, each showing the smart air-surface sterilization system 100 in a surface sterilization mode. FIGS. 7 and 8 are schematic perspective views, each showing the smart air-surface sterilization system 100 in a transition mode from the surface sterilization mode to an air sterilization mode. FIGS. 9 and 10 are schematic perspective views, each showing the smart air-surface sterilization system 100 in the air sterilization mode. FIGS. 11 to 13 are schematic side views when viewed from the arrow direction M (front direction) in FIG. 5. FIGS. 14 to 16 are schematic side views when viewed from the arrow direction N (horizontal direction) in FIG. 5. Each of FIGS. 11 to 16 shows sequentially the transition from the surface sterilization mode to the air sterilization mode. In FIGS. 5 to 16, for the sake of convenience, the illustration of the indoor space 200 is omitted. The transition from the air sterilization mode to the surface sterilization mode has been described with reference to FIGS. 1 and 2. An embodiment of the present disclosure regarding the transition from the surface sterilization mode to the air sterilization mode will be described with reference to FIGS. 5 to 16.

In the smart air-surface sterilization system 100 shown in FIGS. 5 to 16, the lifting member 1 is a plate member. The plate member faces the bottom surface of the indoor space. The lower end of the folding module 20 is rotatably coupled to the upper surface of the lifting member 1. The upper end of the folding module 20 may be fixedly coupled to the ceiling surface of the indoor space.

The smart air-surface sterilization system 100 may further include a ceiling installation member 4 if necessary. The ceiling installation member 4 is integrally fixed and installed at the ceiling surface of the indoor space. The ceiling installation member 4 faces the lifting member 1. The upper end of the folding module 20 may be rotatably coupled and fixed to the lower surface of the ceiling installation member 4. The ceiling installation member 4 may be also a plate member. With the ceiling installation member 4, it becomes easier to install the smart air-surface sterilization system 100 and the lifting member 1.

The folding module 20 includes a first lamp installation member 20a and a second lamp installation member 20b. The first lamp installation member 20a and the second lamp installation member 20b are elongated members. The first and second lamp installation members 20a, 20b are connected rotatably relative to each other by an intermediate hinge 20c. The lower end of the folding module 20 (to be specific, the lower end of the second lamp installation member 20b) is rotatably coupled to the upper surface of the lifting member 1. The upper end of the folding module 20 (to be specific, the upper end of the first lamp installation member 20a) is rotatably coupled to the ceiling surface of the indoor space or the ceiling installation member 4. The UVC lamp 2 is installed in each of the first and second lamp installation members 20a, 20b. The drawings show the UVC lamp 2 in an elongated tube shape. However, the UVC lamp 2 may have any other shape. A plurality of ball-shaped UVC lamps may be arranged in an array in the first and second lamp installation members 20a, 20b.

When the indoor space is in the empty situation, as shown in FIGS. 5, 6, 11 and 14, the lifting member 1 is lifted down close to the bottom surface of the indoor space. Accordingly, the first and second lamp installation members 20a, 20b are vertically extended. At the same time, the UVC lamp 2 is also vertically extended, and faces the wall of the indoor space. In this state, surface sterilization is performed by the UVC radiation from the UVC lamp 2 onto the wall of the indoor space.

When the situation of the indoor space is changed from the empty situation to the occupied situation, as shown in FIGS. 7, 8, 12 and 15, rotation is carried out at the intermediate hinge 20c and the intermediate hinge 20c moves away from the wall of the indoor space. Accordingly, the folding module 20 is gradually bent. Eventually, as shown in FIGS. 9, 10, 13 and 16, the folding module 20 is completely folded. The first and second lamp installation members 20a, 20b and the UVC lamp 2 installed at them are laid in the horizontal direction facing the ceiling surface of the indoor space. In this state, the UVC lamp 2 emits UVC radiation toward the ceiling surface of the indoor space. In parallel to this, when the air circulation fan 3 operates, air in the indoor space flows between the lifting member 1 and the ceiling surface of the indoor space. When the ceiling installation member 4 is included, air in the indoor space flows between the lifting member 1 and the ceiling installation member 4. Air sterilization is performed by the UVC radiation into the flow of air.

Figure 17A:
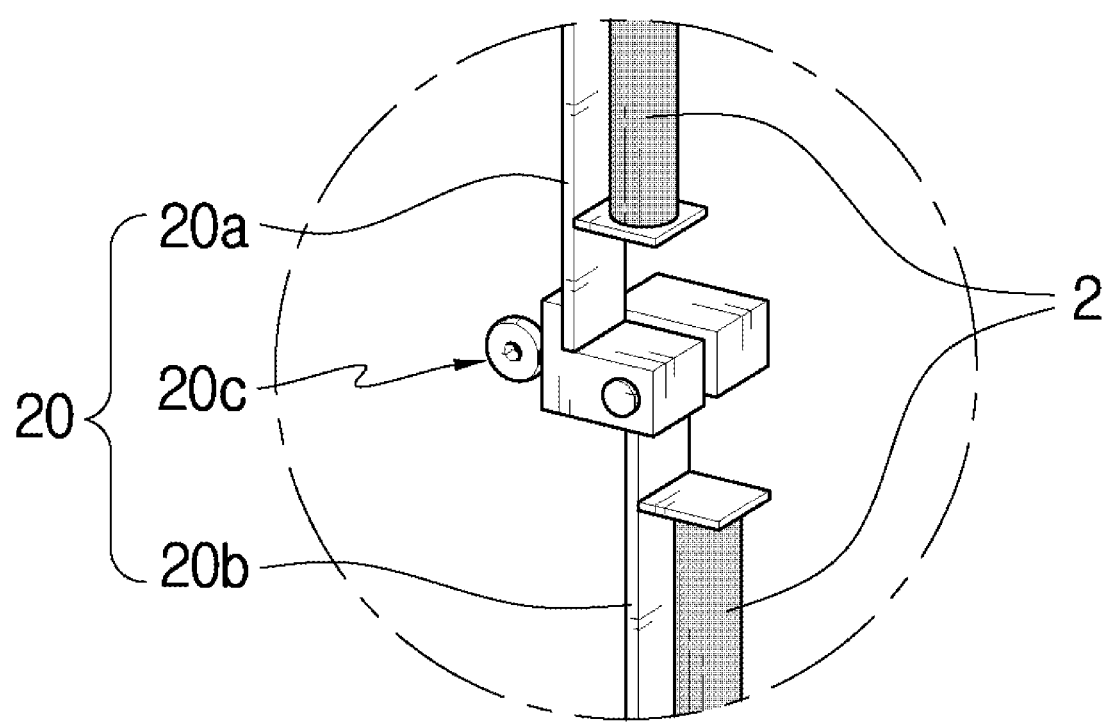
FIGS. 17A to 17C are schematic enlarged views of section A in FIG. 5, showing sequentially the bending of an intermediate hinge of a folding module.
Figure 17B:
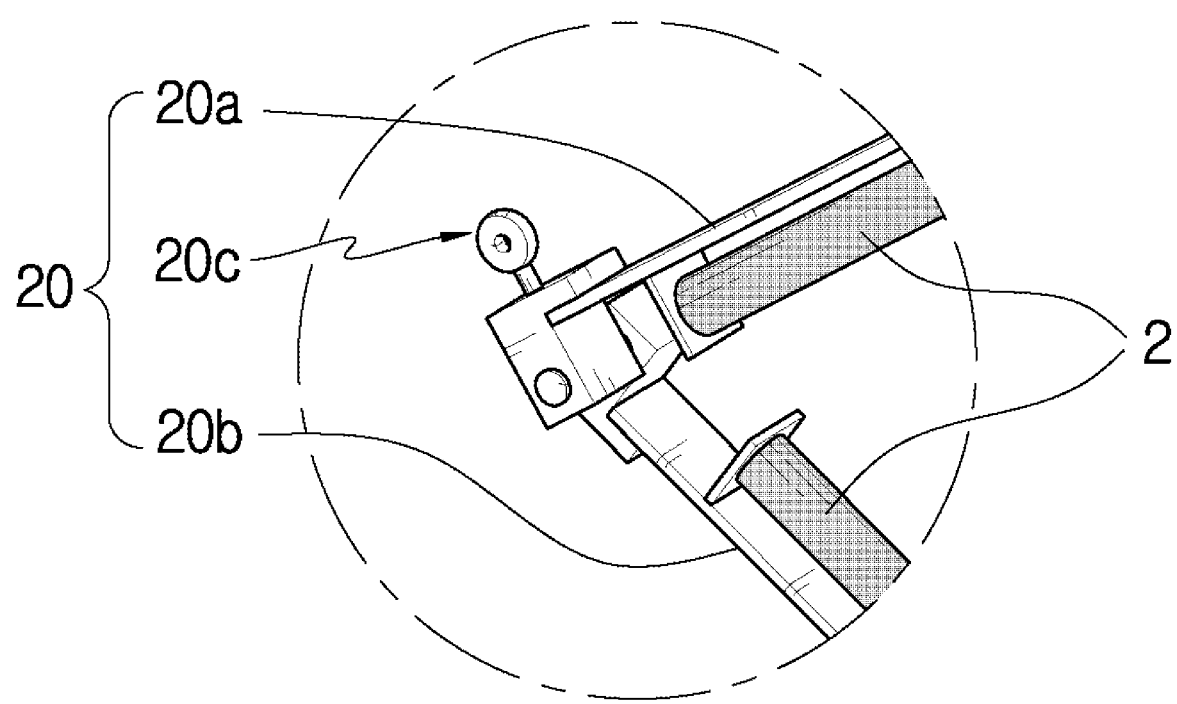
Figure 17C:
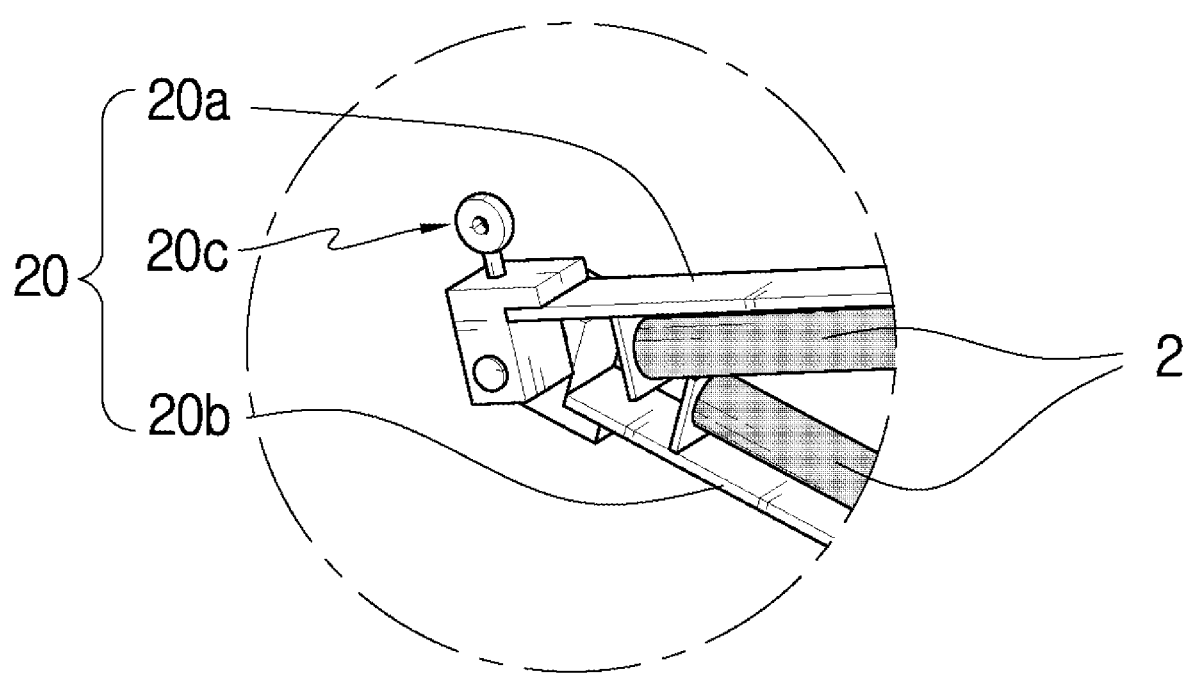

The rotatable intermediate hinge 20c is configured to form a bend between the first and second lamp installation members 20a, 20b. Each of FIGS. 17A to 17C is an enlarged view of section A in FIG. 5. FIGS. 17A to 17C show sequentially the rotation of the intermediate hinge 20c. The lower end of the first lamp installation member 20a and the upper end of the second lamp installation member 20b are rotatably coupled to each other at the intermediate hinge 20c. As shown in FIGS. 17A to 17C, the lower end of the first lamp installation member 20a and the upper end of the second lamp installation member 20b may come into contact with each other in the horizontal plane.

The folding module 20 includes the first and second lamp installation members 20a, 20b and the intermediate hinge 20c. The folding module 20 may be disposed on each of the opposite sides of the lifting member 1. A plurality of folding modules 20 may be arranged at an interval along the side of the lifting member 1. As the plurality of folding modules 20 is positioned, surface sterilization may be performed over the entire wall of the indoor space.

The lifting module may have a wire. The lower end of the wire is connected to the lifting member 1. The upper end of the wire is connected to a winding device. The winding device may be a winch. When the winding device operates to unwind the wire down, the lifting member 1 is vertically lifted down. When the winding device operates to pull the wire, the lifting member 1 is vertically lifted up.

In the embodiment shown in FIGS. 5 to 16, the lower end of the wire 11 is fastened to the intermediate hinge 20c. The lower end of the wire 11 may be coupled to the lower end of the first lamp installation member 20a at the intermediate hinge 20c. In contrast, the lower end of the wire 11 may be coupled to the upper end of the second lamp installation member 20b at the intermediate hinge 20c. The upper end of the wire 11 is wound on the winding device 10. When the wire 11 is pulled by the winding device, the intermediate hinge 20c of the folding module 20 is pulled away from the wall of the indoor space. This configuration achieves the rotating bending at the intermediate hinge 20c of the folding module 20 and its consequential folding effectively and stably.

In the embodiment shown in FIGS. 5 to 16, the plurality of folding modules 20 is arranged at an interval on each of the two opposite sides of the lifting member 1. To bend the plurality of folding modules 20 at the same time, the lower end of the wire 11 is individually coupled to the intermediate hinge 20c of each of the plurality of folding modules 20. Since there is the plurality of wires 11, in the embodiment shown in FIGS. 5 to 16, the winding device 10 includes a winding shaft 12 to which the upper ends of the plurality of wires 11 are coupled at the same time. Since the plurality of folding modules 20 is disposed on each of the two opposite sides of the lifting member 1, two winding shafts 12 are disposed in parallel. The two winding shafts 12 are connected to a central drive shaft 13 by a force transfer member 14 such as a pulley. When the central drive shaft 13 is rotated by a power source 15 such as a motor, the rotational force is transferred to each winding shaft 12 by the force transfer member 14. Additionally, the two winding shafts 12 rotate at the same time. Accordingly, when the plurality of wires 11 connected to the winding shafts 12 is pulled at the same time, the plurality of folding modules 20 is bent at the same time. When the wires 11 are continuously pulled, the folding modules 20 are folded by the rotation at the intermediate hinge 20c as described above.

In the empty situation of the indoor space, the wire 11 is unwound and extended from the winding shaft 12 by the active rotation of the winding shaft 12 or the weight of the lifting member 1. Accordingly, the lifting member 1 is lifted down.

However, in the present disclosure, the configuration of the lifting module is not limited thereto. For example, the wire may be connected to each corner of the lifting member 1, and the winding device may be installed at the ceiling surface of the indoor space or the ceiling installation member 4. Additionally, an extendable/retractable telescopic member may be installed between the ceiling surface and the lifting member 1 or between the ceiling installation member 4 and the lifting member 1, and the lifting member 1 may be lifted up or down by extending or retracting the extendable/retractable member.

What is claimed is:

1. A smart air-surface sterilization system, comprising:
a human body detection sensor to determine an occupied situation or an empty situation of an indoor space;
a lifting member installed in the indoor space;
a lifting module to vertically lift the lifting member up and down;
a folding module installed on the lifting member, wherein the folding module is folded when the lifting member is lifted up and is unfolded when the lifting member is lifted down; and
a Ultra-Violet C (UVC) lamp installed in the folding module,
wherein when the empty situation is determined, the lifting member is lifted down by the lifting module, the folding module is unfolded, and the UVC lamp emits UVC radiation to a wall of the indoor space to perform surface sterilization, and
when the occupied situation is determined, the lifting member is lifted up by the lifting module, the folding module is folded, and the UVC lamp faces a ceiling surface of the indoor space, and emits UVC radiation into air flowing between an upper surface of the lifting member and the ceiling surface of the indoor space to perform air sterilization; and
wherein the lifting member is a plate member which faces a bottom surface of the indoor space,
wherein the smart air-surface sterilization system further comprises a ceiling installation member, wherein the ceiling installation member faces the lifting member and is integrally fixed and installed at the ceiling surface of the indoor space,
wherein the folding module includes first and second lamp installation members, wherein the first and second lamp installation members are elongated members, and are rotatably connected to each other by an intermediate hinge,
wherein an upper end of the first lamp installation member is rotatably coupled to a lower surface of the ceiling installation member,
wherein a lower end of the second lamp installation member is rotatably coupled to the upper surface of the lifting member, and
wherein the UVC lamp is installed in each of the first and second lamp installation members.

2. The smart air-surface sterilization system according to claim 1, wherein the lifting module includes a wire and a winding device to wind or unwind the wire, and
wherein the winding device is configured to unwind the wire down to vertically lift the lifting member down, or pull the wire to vertically lift the lifting member up.

3. The smart air-surface sterilization system according to claim 2, wherein a lower end of the wire is coupled to the lower end of the first lamp installation member or the upper end of the second lamp installation member at the intermediate hinge of the folding module, and
wherein when the wire is pulled, the intermediate hinge rotates away from the wall of the indoor space and the folding module is folded.

4. The smart air-surface sterilization system according to claim 1, wherein a plurality of the folding modules is arranged at an interval on each of two opposite sides of the lifting member.

* * * * *